United States Patent
Chiou et al.

(10) Patent No.: US 8,922,225 B2
(45) Date of Patent: Dec. 30, 2014

(54) SENSING PAD

(75) Inventors: Jin-Chern Chiou, Taichung (TW);
Shih-Che Lo, Taichung (TW);
Hsin-Hsueh Tsai, Taichung (TW);
Jia-Hung Yan, Tainan (TW); Fong Yuan Chang, Taichung (TW); Hui-Mei Chang, Taichung (TW)

(73) Assignee: China Medical University, Taichung (TW)

(*) Notice: Subject to any disclaimer, the term of this patent is extended or adjusted under 35 U.S.C. 154(b) by 272 days.

(21) Appl. No.: 13/491,151

(22) Filed: Jun. 7, 2012

(65) Prior Publication Data
US 2013/0328574 A1 Dec. 12, 2013

(51) Int. Cl.
*G01R 27/28* (2006.01)

(52) U.S. Cl.
USPC .......................................... 324/649; 200/85 R

(58) Field of Classification Search
None
See application file for complete search history.

(56) References Cited

U.S. PATENT DOCUMENTS

| | | | | |
|---|---|---|---|---|
| 2006/0105152 | A1* | 5/2006 | Cok et al. | 428/209 |
| 2008/0007537 | A1* | 1/2008 | Asbill | 345/173 |
| 2008/0169931 | A1* | 7/2008 | Gentry et al. | 340/573.1 |
| 2012/0065547 | A1* | 3/2012 | Hann | 600/587 |
| 2012/0272751 | A1* | 11/2012 | Gorjanc et al. | 73/862.046 |

* cited by examiner

*Primary Examiner* — Melissa Koval
*Assistant Examiner* — Courtney McDonnough
(74) *Attorney, Agent, or Firm* — Muncy, Geissler, Olds & Lowe, P.C.

(57) ABSTRACT

A sensing pad includes a first sensing layer, a second sensing layer and a spacer layer. The second sensing layer has at least one second sparse sensing zone and at least one second dense sensing zone. The spacer layer is disposed between the first sensing layer and second sensing layer, and includes at least one high pressure spacer zone and at least one low pressure spacer zone. The second sensing layer is pressed downwards upon receiving a load to compress the spacer layer and contact the first sensing layer to generate electric connection, thereby detecting the pressed location. Through the dense sensing zone and sparse sensing zone distributed on the second sensing layer whether a person is lay on a bed can be judged to reduce faulty judgments, and the posture of the person can be detected to better understand conditions of the person lay on the bed.

12 Claims, 10 Drawing Sheets

SENSING PAD

FIELD OF THE INVENTION

The present invention relates to a sensing pad and particularly to sensing pad equipped with contact or weight sensors.

BACKGROUND OF THE INVENTION

To many patients and aged people bed is necessary for rest and rehabilitation. Hence many nursing institutions have installed monitoring cameras to monitor whether the patients or aged people have rested on the beds timely to maintain good health and also to understand their sleeping quality and conditions. However, such a scheme makes the people under monitoring uncomfortable mentally and cannot rest easily and also feel intrusion of privacy.

With advances of medical and technology medical equipments have a great deal of improvements in recent years. Now some beds can be equipped with weight sensors on the bed board with four weighing means installed on four legs of the bed, then by calculating through a formula the gravity center location of the person lay on the bed can judge whether the person has left the bed or changed the posture. Such an approach free the bedridden people the uncomfortable feeling of being watched by the monitoring cameras. But the aforesaid technique of judging the posture alteration via deduction of change of the gravity center through a formula could result in a greater range of faulty judgment. It also provides insufficient information in terms of the positional conditions of the person lay on the bed.

SUMMARY OF THE INVENTION

The primary object of the present invention is to solve the problems of greater range of faulty judgment and insufficient information of positional conditions of the person lay on the bed that occurs to the conventional bed mattress equipped with weight sensors.

To achieve the foregoing object the present invention provides a sensing pad which includes a first sensing layer, a second sensing layer and a spacer layer. The second sensing layer has at least one second sparse sensing zone and at least one second dense sensing zone. The spacer layer is disposed between the first sensing layer and second sensing layer, and includes at least one high pressure spacer zone and at least one low pressure spacer zone. The second sensing layer is pressed downwards upon receiving a load to compress the spacer layer and contact the first sensing layer to generate electric connection, thereby detect the pressed location.

Thus, by distributing the at least one dense sensing zone and the at least one sparse sensing zone of the second sensing layer, the dense sensing zone can detect a smaller area while the spare sensing zone can detect a larger area, and through the characteristics of weight contact area of objects, desirable sensing zones can be arranged to make detection in an effective range, thereby to judge whether a person is lay on a bed and also detect person's posture on the bed to reduce faulty judgment and better understand person's conditions in using the bed.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
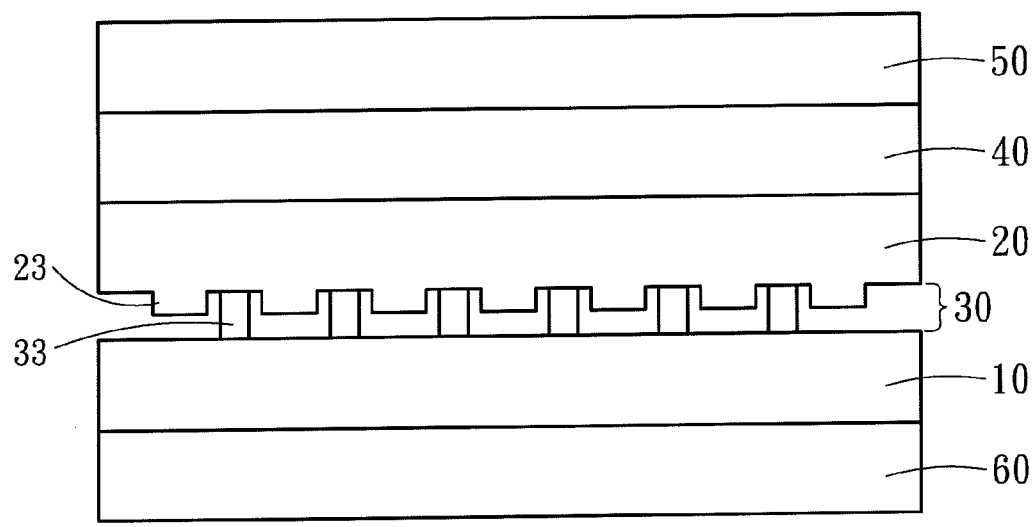
FIG. 1 is a cross section of a first embodiment of the invention.
Figure 2:
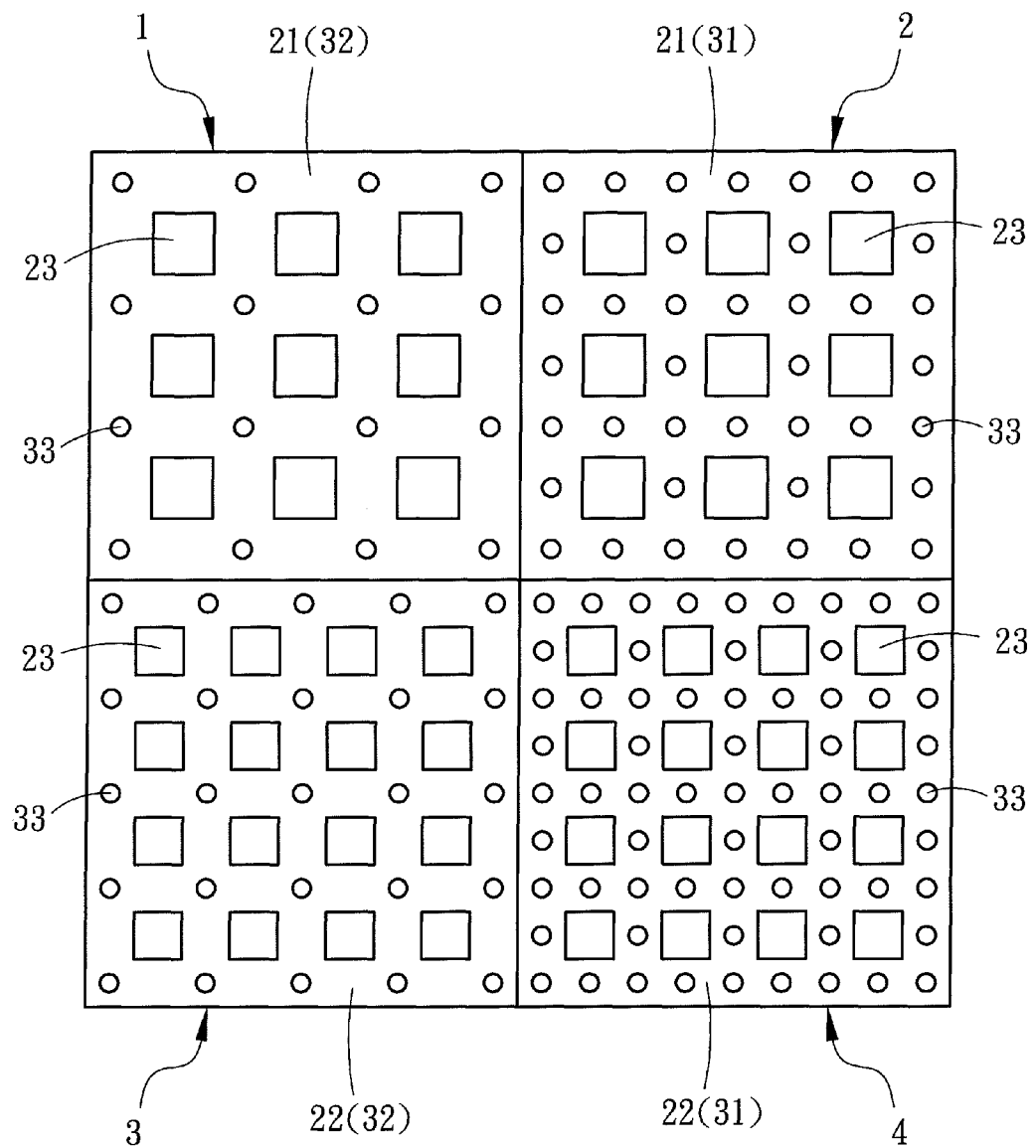
FIG. 2 is a schematic view of an arrangement layout of sensing zones and spacer zones of the first embodiment.

Please refer to FIGS. 1 and 2 for a first embodiment of the sensing pad of the invention. The sensing pad includes a first sensing layer 10, a second sensing layer 20 and a spacer layer 30. The second sensing layer 20 has at least one second sparse sensing zone 21 and at least one second dense sensing zone 22. The spacer layer 30 is disposed between the first sensing layer 10 and second sensing layer 20, and includes at least one high pressure spacer zone 31 and at least one low pressure spacer zone 32. The second sensing layer 20 has a plurality of sensing members 23 located thereon that can be pressed downwards upon receiving a load to compress the spacer layer 30 and contact the first sensing layer 10 to generate electric connection, thereby detect the pressed location.

This embodiment further includes a pliable layer 40 overlapping with the second sensing layer 20 so that the second sensing layer 20 is interposed between the pliable layer 40 and spacer layer 30 to make person lay on the bed to feel more comfortable. Through the pliable layer 40, the load can be applied indirectly to the second sensing layer 20 to detect the location of the person. In addition, a waterproof and air permeable layer 50 may also be added and overlapped with the pliable layer 40 to make the pliable layer 40 interposed between the water and air permeable layer 50 and second sensing layer 20, so that a bedridden person who does not toss around frequently on the bed can be free from inflicting decubitus due to sweltering, and the pliable layer 40 also does not need to be washed frequently for persons who have bed wetting problem. In the event that the sensing pad of the invention is lay on a bedstead which is not a flat board, a rigid layer 60 is added overlapping with the first sensing layer 10 which is interposed between the rigid layer 60 and spacer layer 30. Thereby the second and first sensing layers 20 and 10 can bear the load of the person lay thereon to accurately detect the weighing locations.

Also referring to FIG. 2, the sensing members 23 are lay denser in the second dense sensing zone 22 than in the second sparse sensing zone 21, thus the second dense sensing zone 22 has a greater sensing resolution than the second sparse sensing zone 21 and is more desirable to detect a smaller contact area. The high pressure spacer zone 31 has a plurality of spacers 33 located thereon more densely than in the low pressure spacer zone 32, thus can withstand a greater pressure to prevent damage of the sensing members 23 between the second sensing layer 20 and first sensing layer 10 caused by too heavy of load. Hence the high pressure spacer zone 31 is preferably to be positioned on a heavier loading position. By arranging the second sparse sensing zone 21 and second dense sensing zone 22 incorporated with the high pressure spacer zone 31 and low pressure spacer zone 32, four types of sensing detection zones with different characteristics are generated as follow:

A sensing zone 1: The second sparse sensing zone 21 incorporating with the low pressure spacer zone 32 desirable to detect a larger contact area and a lighter load;

B sensing zone 2: The second sparse sensing zone 21 incorporating with the high pressure spacer zone 31 desirable to detect a larger contact area and a greater load;

C sensing zone 3: The second dense sensing zone 22 incorporating with the low pressure spacer zone 32 desirable to detect a smaller contact area and a lighter load; and D sensing zone 4: The second dense sensing zone 22 incorporating with the high pressure spacer zone 31 desirable to detect a smaller contact area and a greater load.

Figure 3:
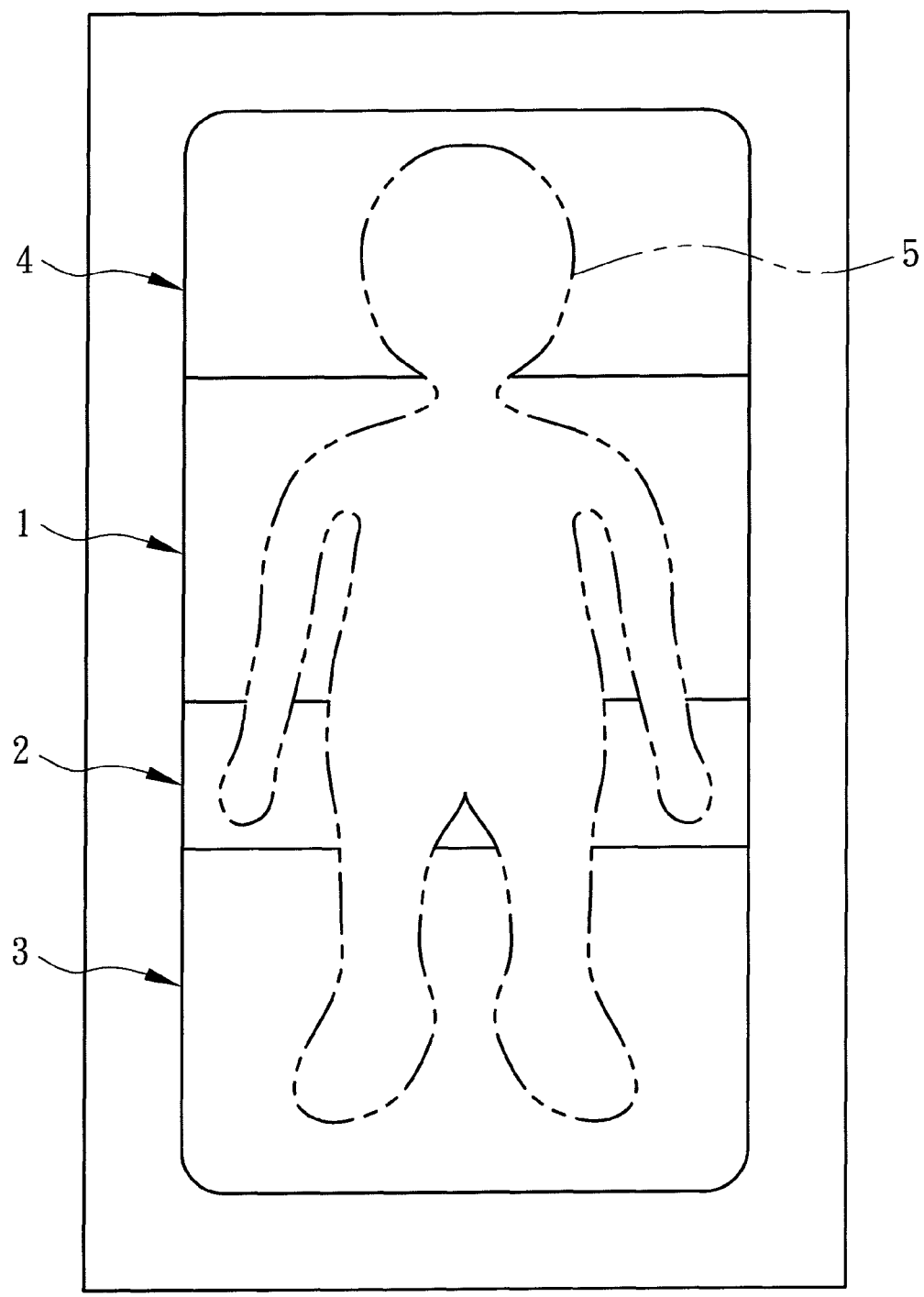
FIG. 3 is a schematic view of an arrangement layout of the sensing zones of the first embodiment.

Please refer to FIG. 3 for a layout of the sensing zones of the first embodiment. In this embodiment the sensing zones are arranged according to a human body 5, from an upper side to a lower side, into a head zone, a back and waist zone, a buttock zone and a leg zone. The head zone requires a smaller sensing area and bears a concentrated load, hence is mated with a D sensing zone 4. The back and waist zone requires a larger sensing area with distributed load, hence is mated with an A sensing zone 1. The buttock zone is the gravity center of the human body and bears the greatest load at a larger area, hence is mated with a B sensing zone 2; and the leg zone requires a smaller sensing area and a smaller load, hence is mated with a C sensing zone 3. Thus, the sensing zones of the sensing pad can be arranged according to the load and area characteristics of the human body 5 to avoid damages of the sensing members 23 caused by too heavy of pressure. Moreover, the second sparse sensing zone 21 can reduce the number of the sensing members 23 needed while providing detection in an effective range.

Figure 4:
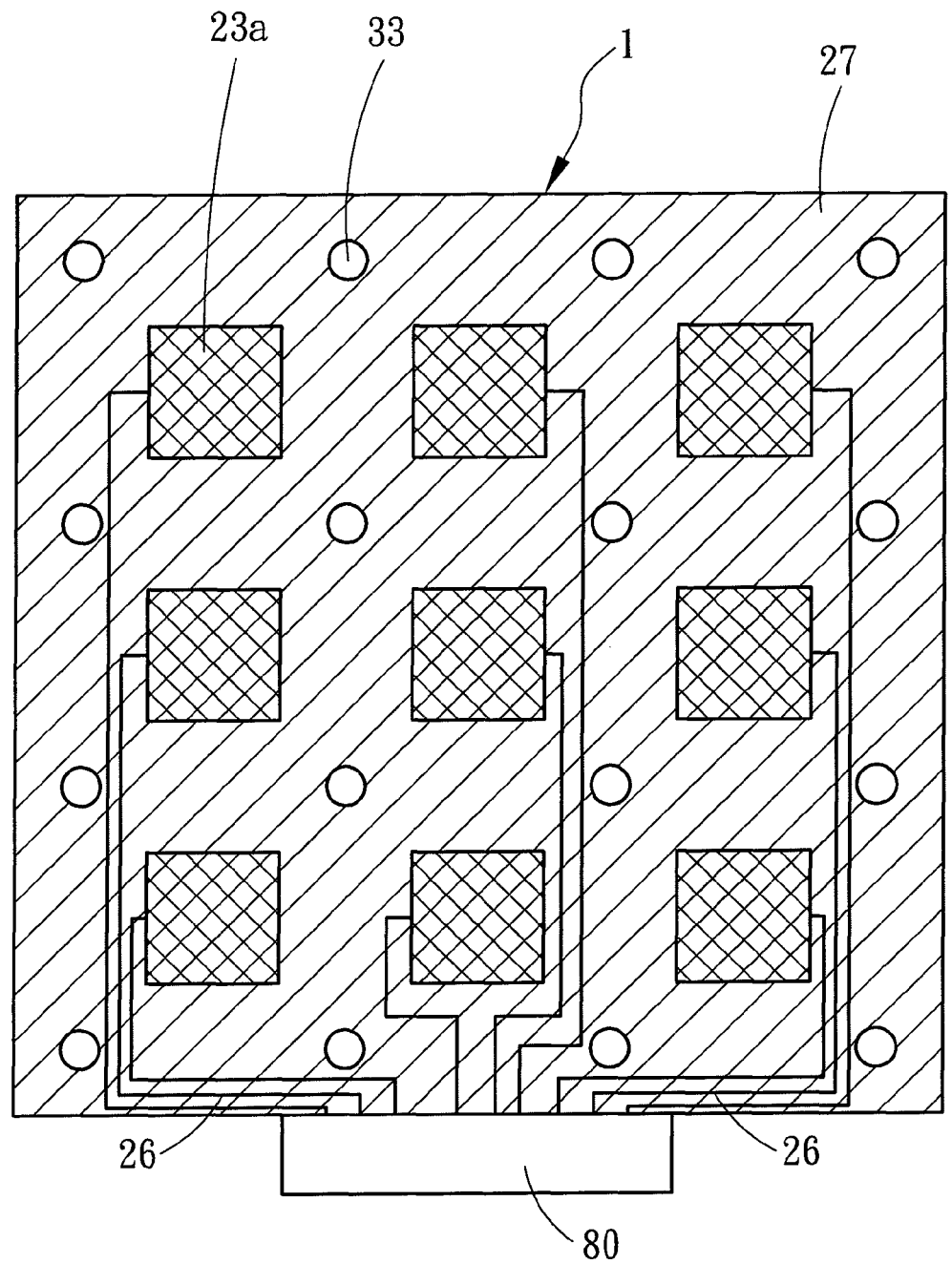
FIG. 4 is a schematic view of the structure sensing member of a second embodiment of the invention.

Please refer to FIG. 4 for a second embodiment of the invention. In this embodiment the sensing members 23a are designed in a lattice structure to reduce the number of the sensing members 23a needed without diminishing the sensing capability. Each sensing member 23a is connected to a detection unit 80 via a second conductive wire 26. The detection unit 80 detects whether the first sensing layer 10 is contact with the second sensing layer 20 through conductive connection of the sensing member 23a, then judge the contact location of user's load on the second sensing layer 20. Moreover, the second conductive wire 26 has an insulation layer 27 to prevent conductive connection between the second conductive wire 26 and first sensing layer 10 when the first sensing layer 10 is overlapped with the second sensing layer 20 to avoid faulty judgment of the detection unit 80.

Figure 5:
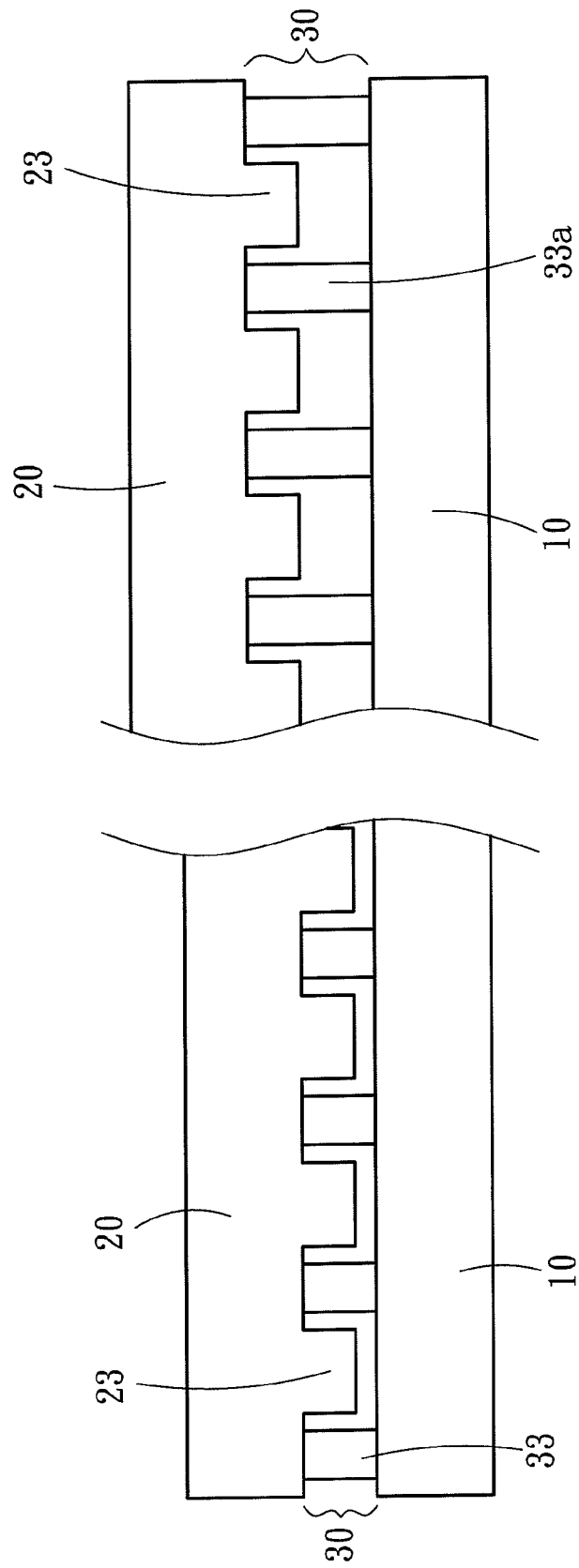
FIG. 5 is a cross section of the spacer structure of a third embodiment of the invention.

Please refer to FIG. 5 for a third embodiment of the invention. Aside from including denser spacers 33 in the high pressure spacer zone 31, other spacers 33a formed at a greater thickness also are provided to increase the contact interval of the second sensing layer 20 and first sensing layer 10, thereby prevent damage of the sensing members 23 caused by over contact due to bearing too heavy of load lay on the second sensing layer 20 and first sensing layer 10.

Figure 6:
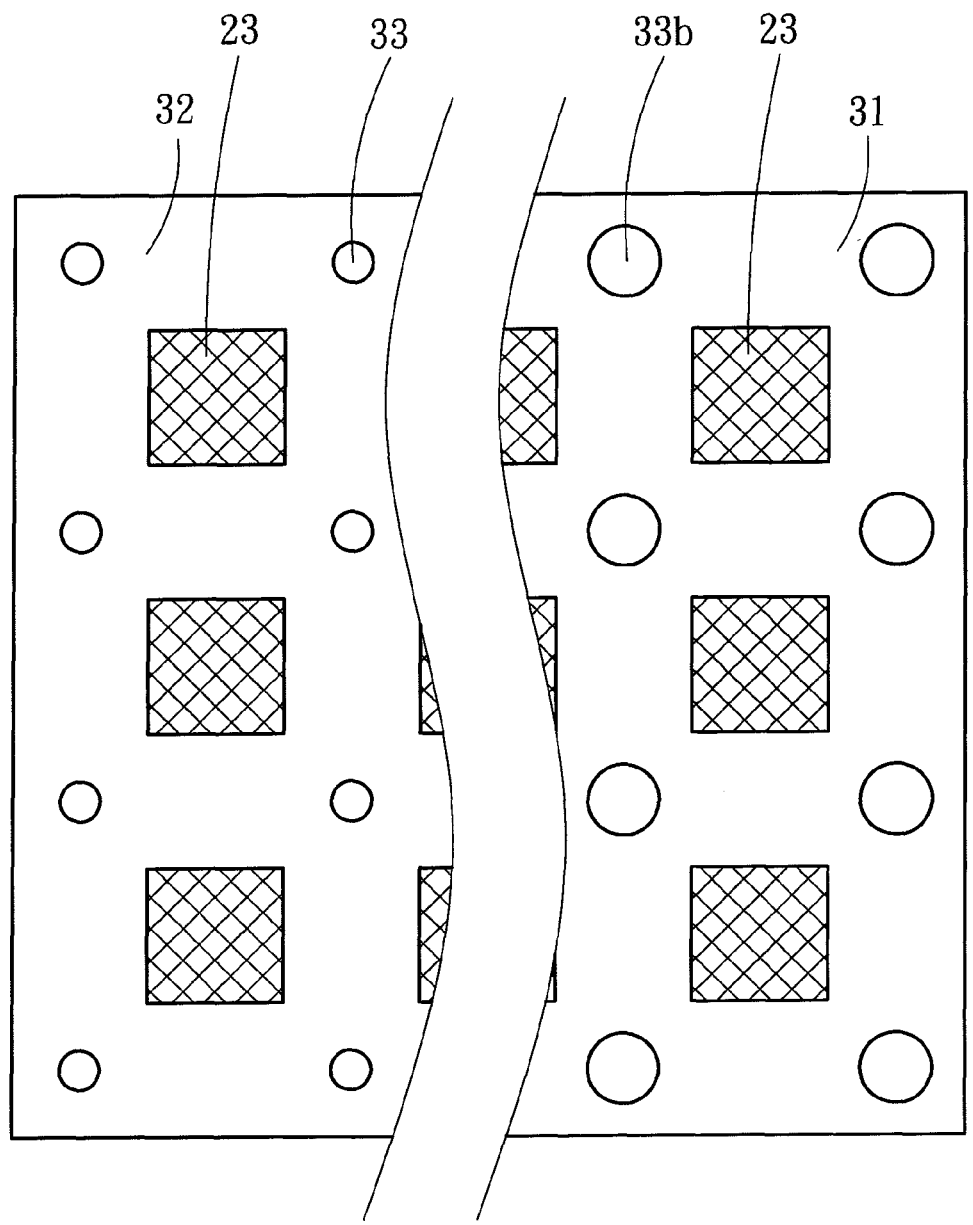
FIG. 6 is a schematic view of the spacer structure of a fourth embodiment of the invention.

Please refer to FIG. 6 for a fourth embodiment of the invention. The spacers 33b located in the high pressure spacer zone 31 have a greater contact area than the spacers 33 located in the low pressure spacer zone 32. The contact area means the contact area of the spacers 33 and 33b with the first and second sensing layers 10 and 20. Such an arrangement allows the spacers 33b in the high pressure spacer zone 31 to bear a greater load, and a greater weight has to be loaded on the high pressure spacer zone 31 to generate sensing for the sensing members 23 located in high pressure spacer zone 31. Moreover, the spacers 33b in the high pressure spacer zone 31 may also be made from material of a greater hardness to achieve the same effect mentioned above by loading a greater weight to generate the sensing for the sensing members 23. In short, by adjusting the distribution density, contact area, thickness and material of the spacers 33, the pressure bearing capability of the corresponding spacer zone can be changed; moreover, the sensitivity in response to the pressure of the sensing members 23 in the spacer zone can also be adjusted indirectly.

Figure 7:
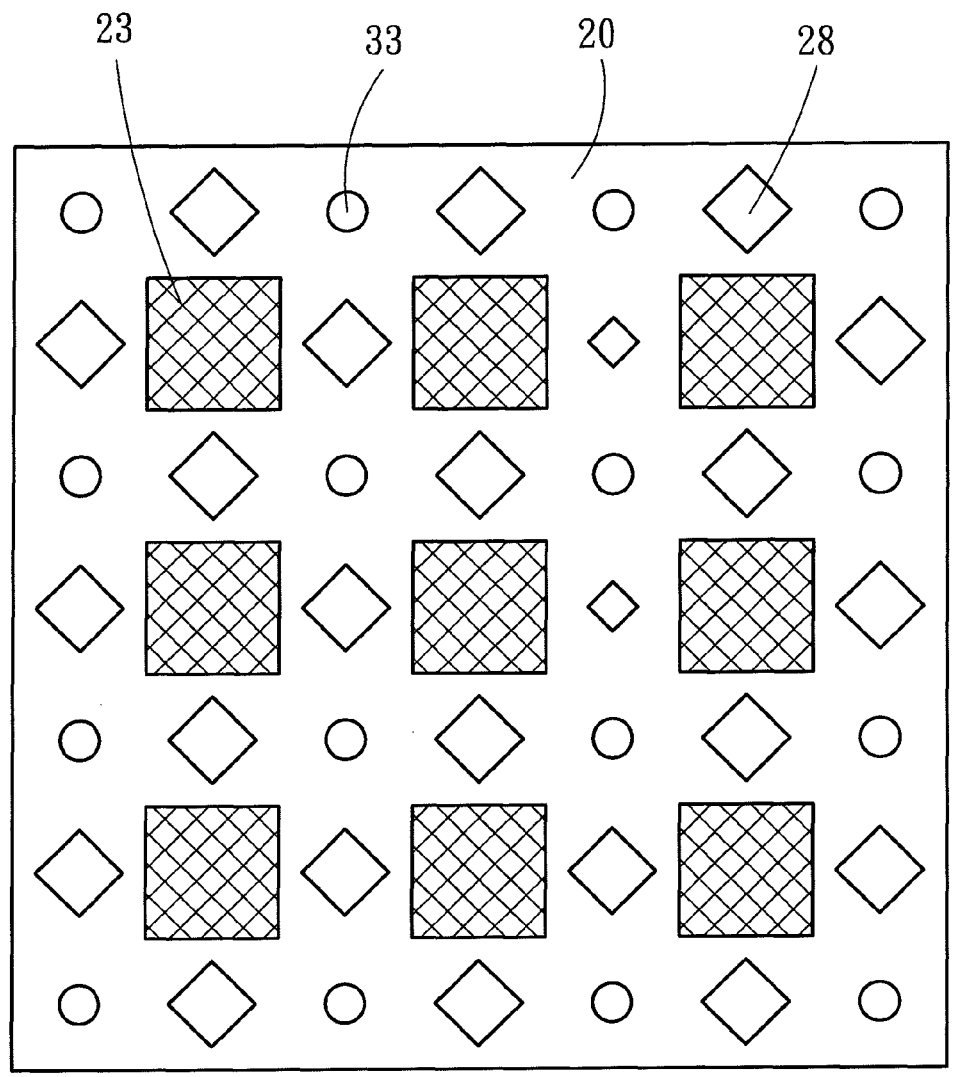
FIG. 7 is a schematic view of apertures distribution of the second sensing layer of a fifth embodiment.

Please refer to FIG. 7 for a fifth embodiment of the invention. In this embodiment the second sensing layer 20 has a plurality of apertures 28 distributed among the sensing members 23 without affecting operation thereof. The apertures 28 can enhance air permeability to improve comfort of the person lay on the pad.

Figure 8:
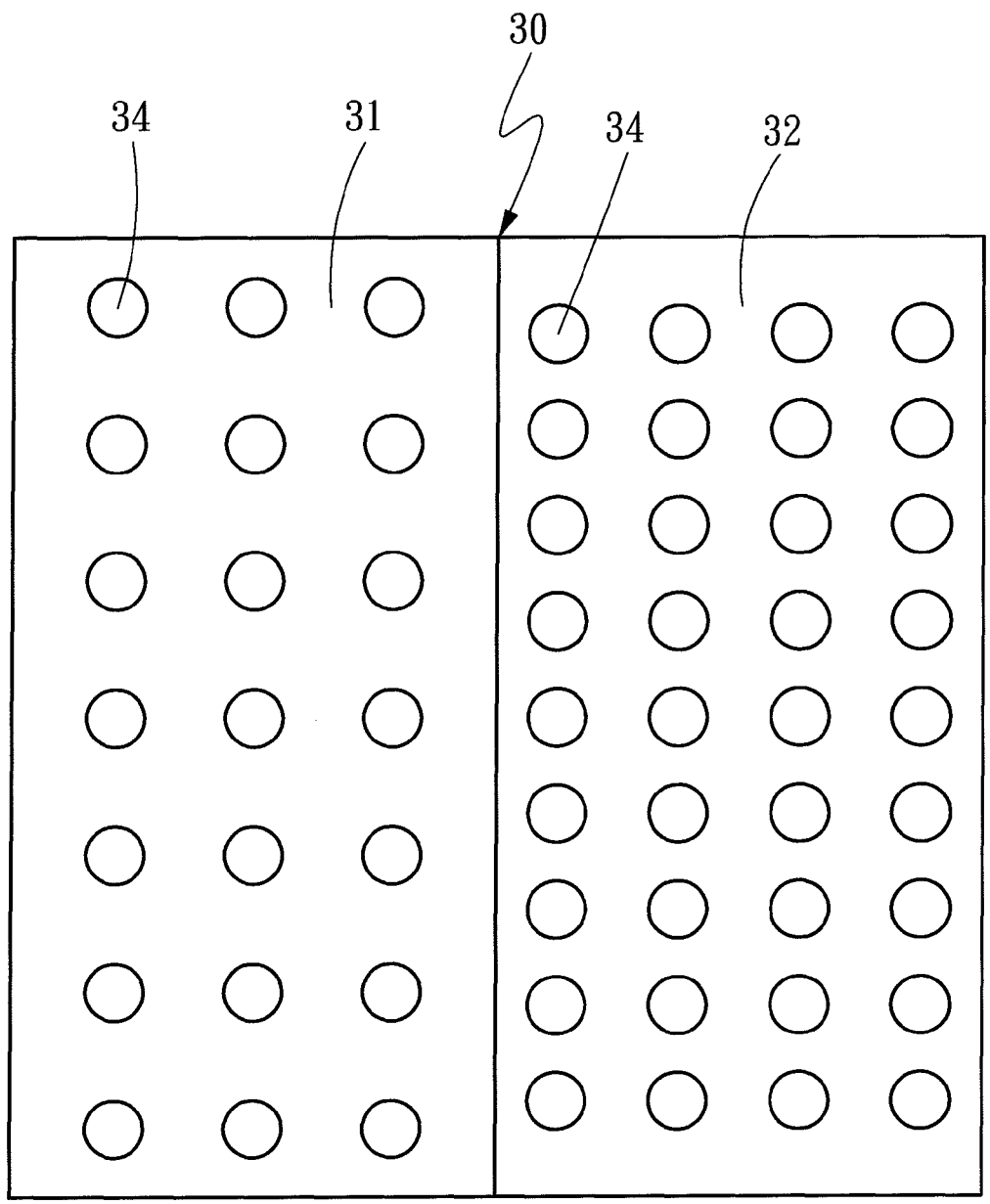
FIG. 8 is a schematic view of the spacer structure of a sixth embodiment of the invention.

Please refer to FIG. 8 for a sixth embodiment of the invention. In this embodiment the spacer layer 30 is a sheet with a plurality of holes 34 formed thereon. When the second sensing layer 20 is pressed downwards upon receiving a load, it contacts the first sensing layer 10 through the holes 34 to form electric connection to detect the press location. The holes 34 in the high pressure spacer zone 31 is distributed sparser than that in the low pressure zone 32, thus the high pressure spacer zone 31 can bear a greater load, while the second sensing layer 20 in the low pressure zone 32 has a higher sensitivity.

Figure 9:
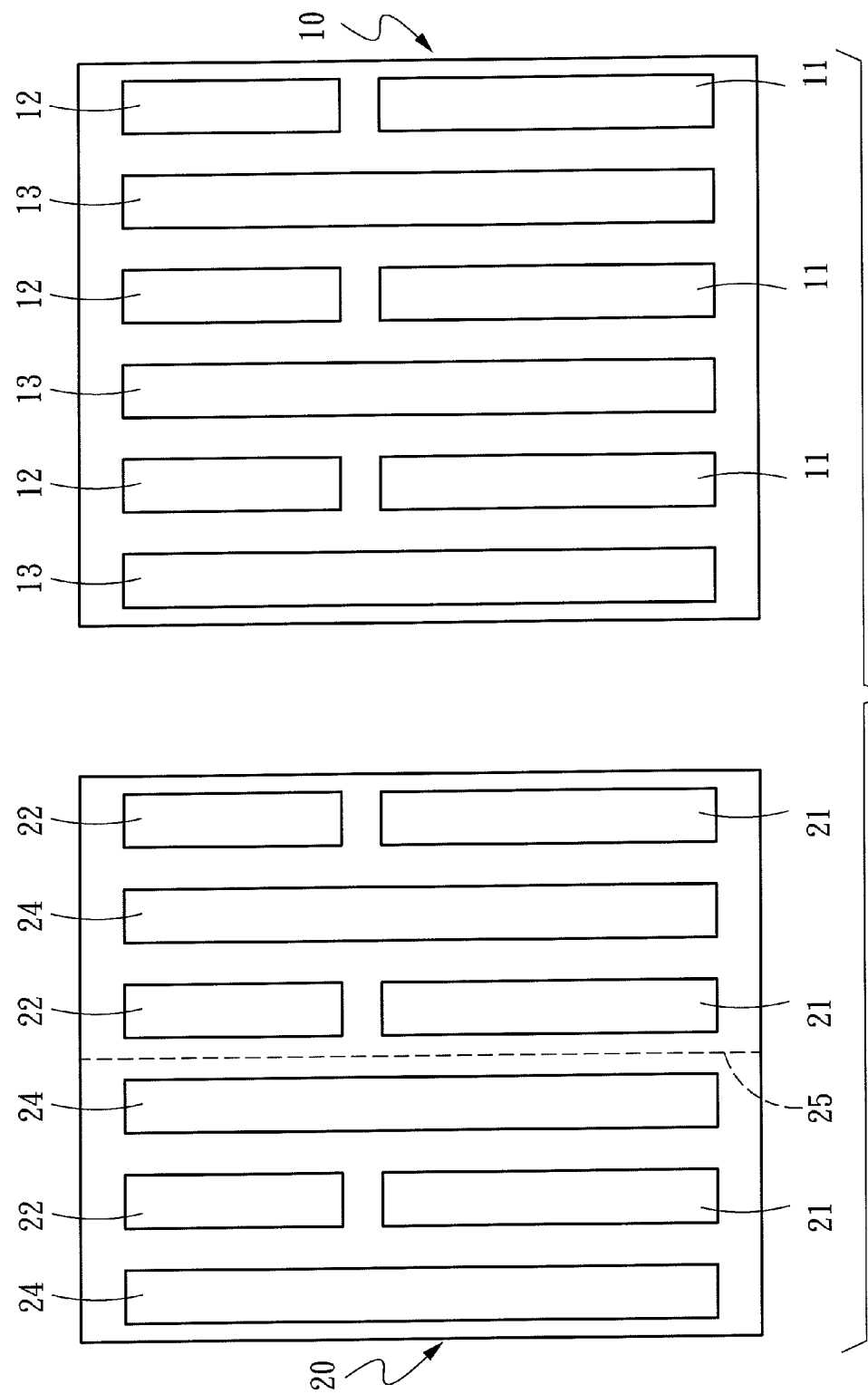
FIG. 9 is a schematic view of sensing zone distribution of a seventh embodiment of the invention.

Please refer to FIG. 9 for a seventh embodiment of the invention. In this embodiment the second sensing layer 20 further includes at least one second corresponding zone 24, and the first sensing layer 10 includes at least one first sparse sensing zone 11, at least one first dense sensing zone 12 and at least one first corresponding zone 13. The first sparse sensing zone 11 and first dense sensing zone 12 are overlapped with the second corresponding zone 24, and the second sparse sensing zone 21 and second dense sensing zone 22 are overlapped with the first corresponding zone 13 so that they are connected to form electric connection upon receiving a load. Through the second sparse sensing zone 21 and second dense sensing zone 22, the contact location can be judged. Similarly, the second corresponding zone 24 contacts the first spare sensing zone 11 and first dense sensing zone 12 to form electric connection when a load is applied thereon, thereby can judge the load contact location via the first spare sensing zone 11 and first dense sensing zone 12.

Therefore, on the second sensing layer 20 the second corresponding zone 24 can be designed in a symmetrical manner against the second sparse sensing zone 21 and second dense sensing zone 22 on the left and right sides through a center axis 25 to make a mold based on the second sensing layer 20 as a model to fabricate two sheets of sensing layers with the sparse sensing zone, dense sensing zone and corresponding zones of the same locations, one sheet is for the first sensing layer 10 and another sheet for the second sensing layer 20. The two sensing layers can be overlapped with each other in a up and down manner with the first sparse sensing zone 11 and first dense sensing zone 12 mating and overlapping with the second corresponding zone 24, and the second sparse sensing zone 21 and second dense sensing zone 22 mating and overlapping with the first corresponding zone 13. Hence only set of mold is needed. Production cost is lower, and the sparse and dense sensing zones can be provided and configured as desired.

Figure 10:
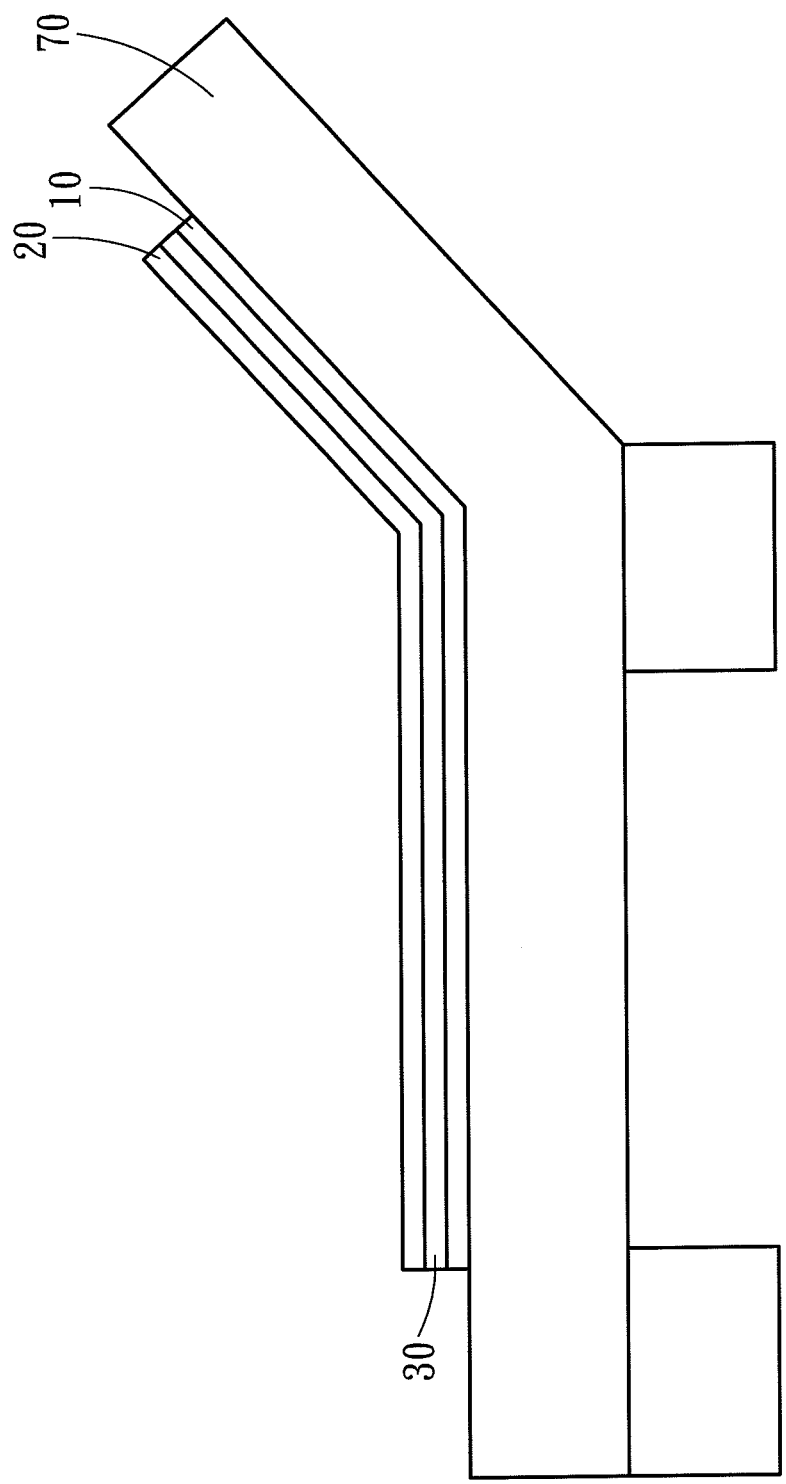
FIG. 10 is a schematic view of the sensing pad of an eighth embodiment of the invention incorporating with a sickbed.

Please refer to FIG. 10 for an eighth embodiment of the invention. Due to a general sickbed 70 now in use can be raised upwards to support a patient to sit up and lift the upper half of body, the first sensing layer 10, second sensing layer 20 and spacer layer 30 can also be made from flexible material to mate the upward folding movement of the sickbed without being damaged by bending.

As a conclusion, the invention, through the sparse sensing zone, dense sensing zone, high pressure spacer zone and low pressure spacer zone, can generate four different types of sensing zones to mate an object which sensing is needed. The invention, not only can judge whether a person is lay on a bed, also can detect the posture of the person on the bed, and reduce faulty judgment and better understand use conditions of the person on the bed. By providing a pliable layer, waterproof and air permeable layer and rigid layer, in addition to the inherent flexibility, it can meet use requirements of the sickbed. By providing a symmetrical structure about the center axis in the sensing zone of the sensing layer, two sets of sensing layers of the same structure can be made to overlap with each other in a up and down manner via only one set of mold to provide a layout with a sparse sensing zone and a dense sensing zone to save production cost.

What is claimed is:

1. A sensing pad, comprising:
   a first sensing layer;
   a second sensing layer disposed above the first sensing layer and including at least one second sparse sensing zone and at least one second dense sensing zone, the second dense sensing zone including a plurality of sensing members arranged denser than that in the second sparse sensing zone so that the second dense sensing zone has a greater sensing resolution than the second sparse sensing zone; and
   a spacer layer disposed between the first sensing layer and the second sensing layer, the spacer layer including at least one high pressure spacer zone and at least one low pressure spacer zone, the second sensing layer being pressed downwards upon receiving a load to compress the spacer layer and contact the first sensing layer to form electric connection, the load needed for pressing the second sensing layer to contact with the first sensing layer in the high pressure spacer zone being greater than that in the low pressure spacer zone.

2. The sensing pad of claim 1, wherein the second sensing layer further includes at least one second corresponding zone, the first sensing layer including at least one first sparse sensing zone, at least one first dense sensing zone and at least one first corresponding zone, the at least one first sparse sensing zone and the at least one first dense sensing zone overlapping with the second corresponding zone and contacting to the second corresponding zone to form electric connection upon receiving the load, the at least one second sparse sensing zone and the at least one second dense sensing zone overlapping with the first corresponding zone and contacting to the first corresponding zone to form electric connection upon receiving the load.

3. The sensing pad of claim 1, wherein the plurality of sensing members are formed in a lattice structure.

4. The sensing pad of claim 3, wherein each of the plurality of sensing members is electrically connected to a detection unit.

5. The sensing pad of claim 1 further including a pliable layer connecting to and overlapping with the second sensing layer, wherein the second sensing layer is interposed between the pliable layer and the spacer layer.

6. The sensing pad of claim 5 further including a rigid layer connecting to and overlapping with the first sensing layer, wherein the first sensing layer is interposed between the rigid layer and the spacer layer.

7. The sensing pad of claim 5 further including a waterproof and air permeable layer connecting to and overlapping with the pliable layer, wherein the pliable layer is interposed between the waterproof and air permeable layer and the second sensing layer.

8. The sensing pad of claim 1, wherein the at least one high pressure spacer zone includes a plurality of spacers arranged denser than that in the at least one low pressure spacer zone.

9. The sensing pad of claim 1, wherein the at least one high pressure spacer zone includes a plurality of spacers formed thicker than that in the at least one low pressure spacer zone.

10. The sensing pad of claim 1, wherein the second sensing layer includes a plurality of apertures for air ventilation.

11. The sensing pad of claim 1, wherein the spacer layer is a sheet, the at least one high pressure spacer zone and the at least one low pressure spacer zone distributing a plurality of holes.

12. The sensing pad of claim 1, wherein the first sensing layer, the second sensing layer and the spacer layer are made from flexible material.

\* \* \* \* \*